(12) United States Patent
Peterson et al.

(10) Patent No.: US 11,024,145 B2
(45) Date of Patent: Jun. 1, 2021

(54) SYSTEM AND METHOD FOR IDENTIFYING VAPING AND BULLYING

(71) Applicant: Soter Technologies, LLC, Hauppauge, NY (US)

(72) Inventors: Derek Peterson, South Setauket, NY (US); William Schweigert, Smithtown, NY (US); Asheik Hussain, Ozone Park, NY (US); Mohammed Elbadry, Port Jefferson Station, NY (US)

(73) Assignee: Soter Technologies, LLC, Ronkonkoma, NY (US)

( * ) Notice: Subject to any disclaimer, the term of this patent is extended or adjusted under 35 U.S.C. 154(b) by 0 days.

(21) Appl. No.: 16/322,175

(22) PCT Filed: Aug. 15, 2018

(86) PCT No.: PCT/US2018/000223
§ 371 (c)(1),
(2) Date: Jan. 31, 2019

(87) PCT Pub. No.: WO2019/035950
PCT Pub. Date: Feb. 21, 2019

(65) Prior Publication Data
US 2020/0402386 A1    Dec. 24, 2020

Related U.S. Application Data

(60) Provisional application No. 62/545,795, filed on Aug. 15, 2017.

(51) Int. Cl.
G08B 21/00    (2006.01)
G08B 21/12    (2006.01)
(Continued)

(52) U.S. Cl.
CPC .............. *G08B 21/12* (2013.01); *A24F 40/51* (2020.01); *G01N 33/005* (2013.01);
(Continued)

(58) Field of Classification Search
CPC .............................. G08B 21/12; H04W 1/129
(Continued)

(56) References Cited

U.S. PATENT DOCUMENTS 3,933,029 A    1/1976  Rabenecker et al.
5,261,596 A    11/1993 Tachibana et al.
(Continued)

FOREIGN PATENT DOCUMENTS

CA    2740454 C    11/2015
GB    2401752 A    11/2004
(Continued)

OTHER PUBLICATIONS

Examination Report No. 1 issued in corresponding Australian Appl. No. 2018316677 dated Aug. 10, 2020 (4 pages).
(Continued)

*Primary Examiner* — Tai T Nguyen
(74) *Attorney, Agent, or Firm* — Carter, DeLuca & Farrell LLP; George Likourezos

(57) ABSTRACT

A sensor system for identifying vaping, other smoking activities, and bullying at a site includes an air quality sensor configured to detect air quality, a sound detector configured to detect sounds, and a network interface configured to transmit a signal indicating abnormality matching signature of vaping, other smoking activity, or sound of bullying. Vaping or another smoking activity is identified based on the detected air quality, and bullying is identified based on the detected sound.

44 Claims, 7 Drawing Sheets

(51) Int. Cl.
  *G06N 20/00* (2019.01)
  *G01N 33/00* (2006.01)
  *G08B 3/10* (2006.01)
  *G08B 5/38* (2006.01)
  *G08B 7/06* (2006.01)
  *H04W 4/029* (2018.01)
  *A24F 40/51* (2020.01)
  *A61B 5/00* (2006.01)

(52) U.S. Cl.
  CPC ......... *G01N 33/0031* (2013.01); *G06N 20/00* (2019.01); *G08B 3/10* (2013.01); *G08B 5/38* (2013.01); *G08B 7/06* (2013.01); *H04W 4/029* (2018.02); *A61B 5/4818* (2013.01)

(58) Field of Classification Search
  USPC ..... 340/540, 541, 575, 576, 628, 630, 632.2
  See application file for complete search history.

(56) References Cited

U.S. PATENT DOCUMENTS

| | | | |
|---|---|---|---|
| 5,451,929 | A | 9/1995 | Adelman et al. |
| 5,856,780 | A | 1/1999 | McGeehin |
| 6,208,252 | B1 | 3/2001 | Danilychev |
| 6,711,470 | B1 | 3/2004 | Hartenstein et al. |
| 6,998,991 | B1 | 2/2006 | Goldstein et al. |
| 7,588,726 | B1 * | 9/2009 | Mouradian .......... G01N 1/2205 422/83 |
| 8,175,297 | B1 | 5/2012 | Ho et al. |
| 9,311,807 | B2 * | 4/2016 | Schultz ............... G06F 13/4221 |
| 2002/0152792 | A1 | 10/2002 | Wang et al. |
| 2005/0199735 | A1 | 9/2005 | Eisenhour et al. |
| 2008/0300817 | A1 | 12/2008 | Bieswanger et al. |
| 2010/0127865 | A1 | 5/2010 | Marriam et al. |
| 2013/0255482 | A1 | 10/2013 | Goodson |
| 2013/0284192 | A1 | 10/2013 | Peleg et al. |
| 2014/0202787 | A1 | 7/2014 | Richardson et al. |
| 2014/0260692 | A1 | 9/2014 | Sharp |
| 2014/0361901 | A1 | 12/2014 | Hoefer |
| 2015/0020614 | A1 | 1/2015 | Gettings et al. |
| 2015/0097678 | A1 | 4/2015 | Sloo et al. |
| 2015/0153171 | A1 | 6/2015 | Zhou et al. |
| 2015/0235652 | A1 | 8/2015 | Moser |
| 2015/0241993 | A1 | 8/2015 | Gallo et al. |
| 2015/0256355 | A1 | 9/2015 | Pera et al. |
| 2015/0323427 | A1 | 11/2015 | Sharp |
| 2016/0050037 | A1 | 2/2016 | Webb |
| 2016/0063841 | A1 | 3/2016 | Schultz et al. |
| 2016/0102879 | A1 | 4/2016 | Guest et al. |
| 2016/0163168 | A1 | 6/2016 | Brav et al. |
| 2016/0212828 | A1 | 7/2016 | Leinen et al. |
| 2016/0260513 | A1 | 9/2016 | Pan et al. |
| 2017/0023457 | A1 | 1/2017 | Hart et al. |
| 2017/0042247 | A1 | 2/2017 | Xiang |
| 2017/0055572 | A1 | 3/2017 | Utley et al. |
| 2017/0227508 | A1 | 8/2017 | Cai et al. |
| 2017/0284690 | A1 | 10/2017 | Lipanov |
| 2017/0309091 | A1 | 10/2017 | Cameron et al. |
| 2017/0321923 | A1 | 11/2017 | Wiens-Kind et al. |
| 2018/0050230 | A1 | 2/2018 | Toland |
| 2018/0195987 | A1 * | 7/2018 | Hur ....................... G08B 25/10 |
| 2018/0286208 | A1 | 10/2018 | Baker et al. |
| 2019/0108739 | A1 | 4/2019 | Wedig et al. |
| 2020/0011779 | A1 | 1/2020 | Lavrovsky et al. |

FOREIGN PATENT DOCUMENTS

| | | |
|---|---|---|
| KR | 101778681 B1 | 9/2017 |
| WO | 2019035950 A1 | 2/2019 |
| WO | 2020005431 A1 | 1/2020 |

OTHER PUBLICATIONS

Office Action issued by the U.S. Patent and Trademark Office dated Jul. 17, 2020 in corresponding U.S. Appl. No. 16/824,347.
Office Action issued by the U.S. Patent and Trademark Office dated Apr. 27, 2020 in corresponding U.S. Appl. No. 16/812,969.
The MagPi Magazine, "Raspberry PI 3: Specs, Benchmarks & Testing," Dec. 31, 2016, retrieved on Apr. 19, 2019 from https://www.raspberrypi.org/magpi/raspberry-pi-3-specs-benchmarks/.
International Search Report and Written Opinion issued by the U.S. Patent and Trademark Office acting as International Searching Authority in International Application No. PCT/US2019/018532 dated May 1, 2019.
International Preliminary Report on Patentability dated Feb. 18, 2020 by the U.S. Patent and Trademark Office acting as International Searching Authority in corresponding International Application No. PCT/US2018/000223.
Notice of Allowance issued by the U.S. Patent and Trademark Office dated Aug. 3, 2020 in corresponding U.S. Appl. No. 16/812,969.
PCT International Search Report & Written Opinon corresponding to PCT Application No. PCT/US18/00223 dated Nov. 15, 2018, 11 pages.
Australian Examination Report No. 2 issued in corresponding Appl. No. AU 2018316677 dated Feb. 10, 2021 (7 pages).
Extended European Search Report issued in corresponding application EP 18846742.7 dated Mar. 30, 2021 (12 pages).

* cited by examiner

SYSTEM AND METHOD FOR IDENTIFYING VAPING AND BULLYING

CROSS REFERENCE TO RELATED APPLICATION

The present application claims the benefit of and priority to PCT Application No. PCT/US18/00223 dated Aug. 15, 2018 which claims priority to U.S. Provisional Application No. 62/545,795, filed on Aug. 15, 2017, the entire contents of both applications are incorporated herein by reference.

BACKGROUND

Technical Field

The present disclosure relates to a system and method for identifying vaping and bullying at an enclosed site. More particularly, the present disclosure relates to a sensor system which includes an air quality sensor for detecting air quality and a sound sensor for detecting sounds.

Background of Related Art

Vaping and bullying have been serious problems in enclosed areas of academic/business environments due to hazardous/harmful impacts on people. Various methods and systems have been developed to identify or prevent bullying and vaping in enclosed areas, such as classrooms, restrooms, bathrooms, storage rooms, hospital rooms, or other kinds of enclosed areas in a school, hospital, warehouse, cafeteria, offices, financial institutes, governmental buildings, or any business entities. For example, bullying and vaping/smoking can be identified by camera surveillance. However, such camera surveillance systems have not been used in private areas such as restrooms, bathrooms, shower rooms, or hospital rooms because privacy has more weights than identification of bullying and vaping/smoking.

Bullying can be detected by a sound sensor at the site. However, there are many other sounds (e.g., flushing, conversions, cleaning, gaming, or sounds from outside) preventing from identification of bullying. Thus, further developments are needed in identification of bullying at enclosed sites.

Vaping becomes more popular in young aged people and causes many health and environmental issues. Generally, vaping has similar effects on people around in close proximity of the smokers. Thus, by identifying vaping or other smoking activities in enclosed areas, people can be supervised appropriately so that harmful and hazardous effects can be prevented. Accordingly, effective identification of vaping/smoking and bullying is in dire need in academic/business environments for safety and public health purposes.

SUMMARY

The present disclosure features a sensor system and an identification system, which includes an air quality sensor and a sound sensor for identifying vaping and bullying.

In an embodiment, a sensor system for identifying vaping, other smoking activities, and bullying at a site includes an air quality sensor configured to detect air quality, a sound detector configured to detect sounds, and a network interface configured to transmit a signal indicating abnormality matching signature of vaping, other smoking activity, or sound of bullying. The vaping or another smoking activity is identified based on the detected air quality, and the bullying is identified based on the detected sound.

In an aspect, the sensor system is powered via power over Ethernet or power over Ethernet+. The power is supplied by a CAT5, CAT5E, or CAT6 cable. The detected air quality and the detected sounds are transmitted wirelessly or via the CAT5, CAT5E, or CAT6 cable.

In another aspect, the vaping or the another smoking activity is identified when the detected air quality includes a signature. The signature includes a temperature range, a hydrogen range, and a humidity range.

In yet another aspect, the air quality sensor is location-independent.

In yet another aspect, the sound detector is location-dependent. The sound detector is to detect sounds in a predetermined period in a learning mode prior to identification of the bullying. The detected sounds during the predetermined period generate base data for identifying the bullying at the site. The bullying is identified when the detected sounds are greater than or equal to a threshold value based on the environment calibrated data.

In yet another aspect, an alert is transmitted silently from the site to a user when the vaping, or another smoking activity, or bullying is detected. The alert is a text message, an email, an optical flashing, an audible sound, or combination thereof.

In still yet another aspect, the sensor system is run by a mobile operating system.

In another embodiment, an identification system for identifying vaping, other smoking activities, and bullying includes a sensor system disposed at a site and a controller coupled to the sensor system via a network. The sensor system includes an air quality sensor configured to detect air quality, a sound detector configured to detect sounds, and a network interface configured to transmit a signal indicating abnormality matching signature of vaping, other smoking activity, or sound of bullying. The controller is configured to identify vaping or another smoking activity based on the sensed air quality, to identify bullying based on the detected sounds, and to send an alert to a user.

In an aspect, the sensor system is powered via power over Ethernet or power over Ethernet+. The power is supplied by a CAT5, CAT5E, or CAT6 cable. The detected air quality and the detected sounds are transmitted wirelessly or via the CAT5, CAT5E, or CAT6 cable.

In another aspect, the vaping or the another smoking activity is identified when the detected air quality includes a signature. The signature includes a temperature range, a hydrogen range, and a humidity range.

In yet another aspect, the air quality sensor is location-independent.

In yet another aspect, the sound detector is location-dependent. The sound detector is to detect sounds in a predetermined period in a learning mode prior to identification of the bullying. The detected sounds during the predetermined period generate base data for identifying the bullying at the site. The bullying is identified when the detected sounds are greater than or equal to a threshold value based on the environment calibrated data.

In yet another aspect, an alert is transmitted silently from the site to a user when the vaping, or another smoking activity, or bullying is detected. The alert is a text message, an email, an optical flashing, an audible sound, or combination thereof.

In still yet another aspect, the sensor system is run by a mobile operating system.

BRIEF DESCRIPTION OF THE DRAWINGS

A better understanding of the features and advantages of the disclosed technology will be obtained by reference to the following detailed description that sets forth illustrative embodiments, in which the principles of the technology are utilized, and the accompanying drawings of which.

DETAILED DESCRIPTION

This disclosure relates to identification systems and detection sensors for detecting air quality and sound to identify whether bullying and vaping (or other smoking activities) occurs at enclosed sites. When bullying and/or vaping are identified, warnings or alerts are transmitted to registered users or clients without providing any indication of warnings to one or more persons who vape or bully at the site. In this way, one or more persons who bully or vape can be properly reported and appropriately supervised later. Further, one or more persons near the vaping or bullying can be effectively prevented from further harms.

Figure 1:
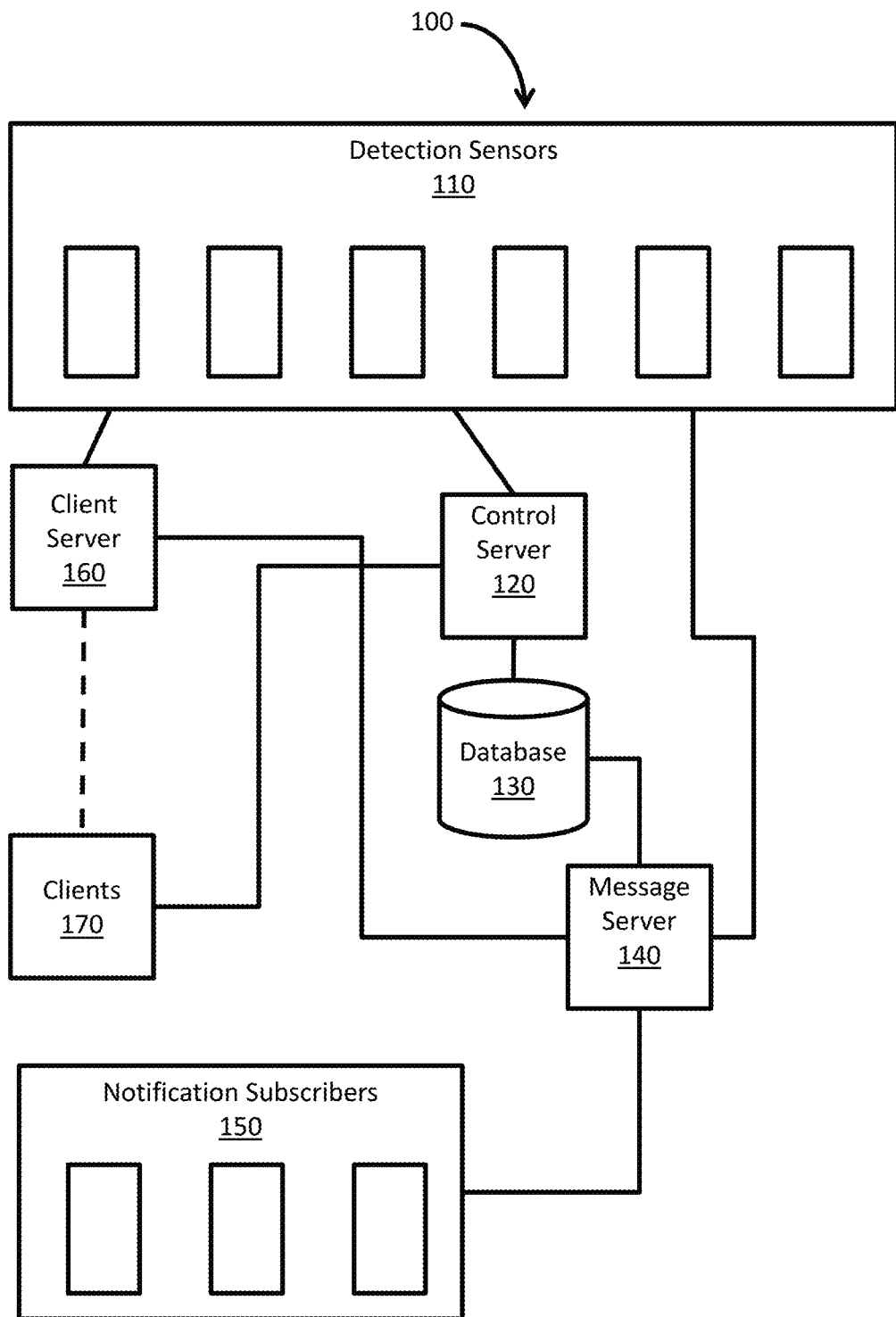
FIG. 1 is a block diagram of an identification system for identifying bullying and vaping/smoking in accordance with embodiments of the present disclosure.

FIG. 1 illustrates a block diagram showing an identification system 100 according to embodiments of the present disclosure. The identification system 100 includes a plurality of detection sensors 110, which detect air quality related to vaping and sound related to noise disturbance at enclosed sites. The identification system 100 further includes a control server 120 for identifying whether or not vaping or bullying occurs at the enclosed site, and a database 130 storing base data for identifying bullying and history data of detected sounds and air quality at each enclosed site.

The detected air quality may be analyzed by the detection sensors 110 or the detected air quality may be transmitted to the control server 120 together with the detected sound. The control server 120 may analyze the detected sound based on base data stored at the database 130 and the detected air quality, and determine whether bullying and/or vaping occurs at the enclosed sites. The base data stored at the database 130 may be location-dependent, meaning that the base data for one location is different from that for another site. The location-dependent base data may be sound data related to identifying bullying. For example, at a bathroom, there are flushing sounds, conversions, cleaning sounds, and etc. Based on the size of the bathroom and the installation location of the detection sensor 110, the detection sensor 110 may detect sounds differently from other detection sensors 110 installed at the bathroom or at a bedroom near the bathroom. Thus, the location-dependent base data may be different based on the installation locations at the same site.

For these reasons, the location-dependent base data is to be obtained at the site for a period in a learning mode. The period may vary depending on the installation location, the time, the day of the week, and the date. The location-dependent base data may be obtained for a period, which is determined based on the environment of the enclosed site and the installation location of the detection sensor 110. After obtaining location-dependent base data for a period sufficiently long enough to form profile for the location, the detection sensor 110 may be turned into an active mode to identify noise disturbance.

In an aspect, when the detection sensor 110 transmits detected results to the control server 120, the control server 120 may acquire from the database 130 the profile for the location where the detection sensor 110 is installed and the time when the detected results is obtained, and analyzes the detected results to identify occurrence of bullying based on the base data.

In an aspect, the detected sounds may be used to identify sleep apnea. Sleep apnea is a serious sleep disorder that occurs when a person's breathing is interrupted while sleeping. People with untreated sleep apnea stop breathing repeatedly during their sleep. This means the brain and the rest of the body may not get enough oxygen. Sleep apnea can lead to more serious problems such as high blood pressure, stroke, heart failure, and diabetes.

Similar to bullying, base data for sleep apnea may be obtained during the learning mode prior to identifying sleep apnea. During the learning mode, the detection sensor 110 may record decibel levels of the sleeping sounds of a person over a temporal period, which may be more or less than one week. The base data may contain patterns of the person's breathing at times when the lulls in breathing and loud spikes occur.

In another aspect, the detection sensor 110 may save the base data in a memory (which is not shown) of the detection sensor 110. In other words, the detection sensor 110 may determine vaping, bullying, or sleep apnea by itself at the site where the detection sensor 110 is installed. In this case, the detection sensor 110 transmits signals indicating abnormality matching signature of vaping, bully, or apnea. This ensures data privacy, meaning that the data stay within the detection sensor 110, and further ensures privacy of people at the site.

During the active mode, the detection sensor 110 may listen to the person's sleeping sounds and the control server 120 may compare the current levels (e.g. decibels) of the sleeping with the expected level from the base data at the corresponding time. The comparing data may be displayed so that the user can see when sleep apnea occurs. The control server 120 may measure anomalies in sound over a predicted norm. The control server 120 may determine patterns of snoring, breathing, or any sound disruption during the sleep by analyzing the sound amplitude pattern that occurs. By analyzing the amplitude of the sound as well as irregular levels of sound in the sleep pattern, the control server 120 may identify sleep apnea.

In an aspect, the base data may be location-independent, meaning that the base data is the same for every enclosed location at every time. The location-independent base data may be air quality data related to identifying vaping. Since vaping has a signature in temperature, humidity, and hydrogen ranges, vaping may be identified based on the signature. In an aspect, features for identifying vaping may be integrated into the detection sensor 110 so that the detection sensor 110 may request an alert or warning message to be sent to the clients 170, when the signature is identified in the detected air quality. The signature may include combination of predetermined ranges of temperature, humidity, and hydrogen.

Generally, hydrogen sensors require at least 7 volts and about 1,000 ohm resistance. The detection sensor 110, however, may have a modified hydrogen sensor, which requires much lower voltage and a much higher resistance. The voltage and resistance may vary based on temperature of the environment.

The database 130 may further include history data which is time-series and location-specific data for identifying bullying for each location where the detection sensor 110 has been installed. In an aspect, the control server 120 may analyze the history data to predict occurrences of vaping and bullying at the location so that appropriate actions may be proactively and precautiously taken at the location.

In an aspect, the control server 120 may analyze the history data stored at the database 130 to identify trend of the history data. The trend may be a decrease or increase pattern of occurrences of vaping or bullying. In case a decrease or increase pattern is identified, the control server 120 may adjust the base data for identifying bullying to make the detection sensor 110 more or less sensitive to the identification. In this way, the base data may be adjusted based on the trend of the history data.

Figure 3A:
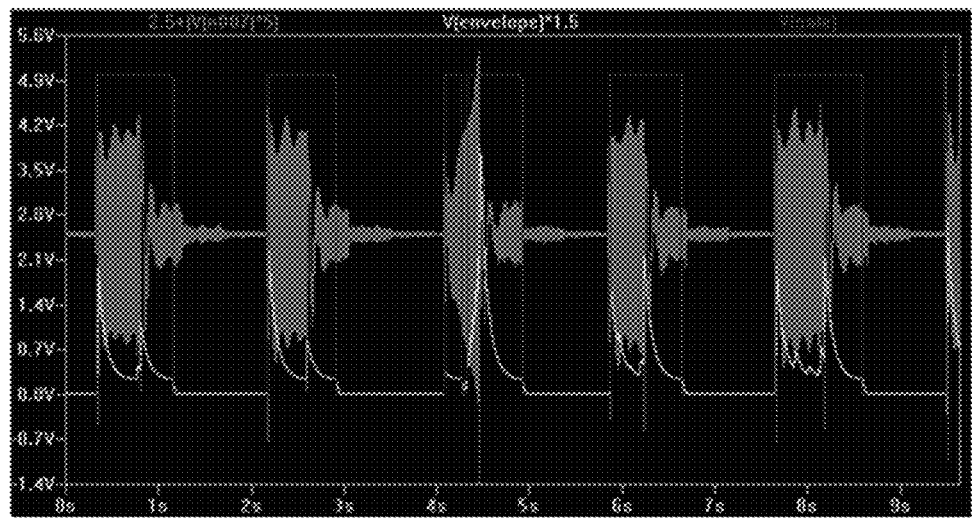
FIG. 3A is a graphical illustration showing detected sound results from the detection sensor of FIG. 1 in accordance with embodiments of the present disclosure.
Figure 3B:
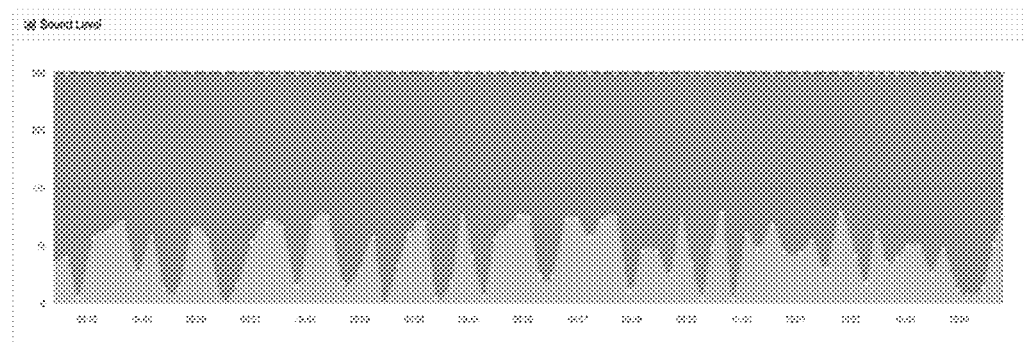
FIGS. 3B and 3C are graphical illustration showing history data from the detection sensor of FIG. 1 in accordance with embodiments of the present disclosure.
Figure 3C:
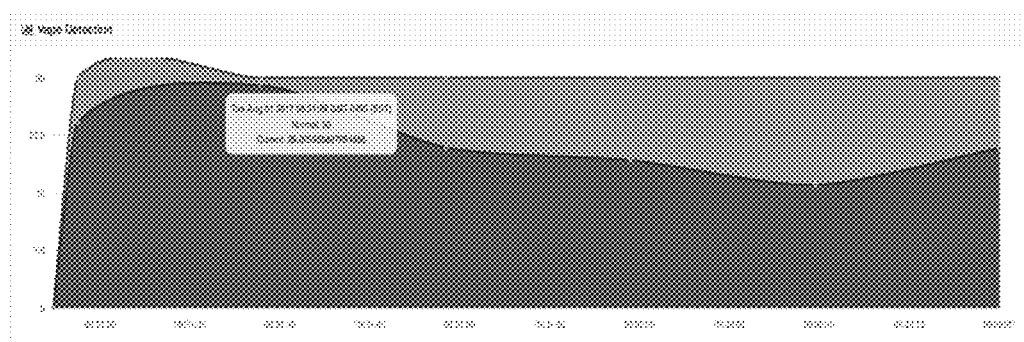

For example, FIGS. 3B and 3C show history data of detected sound level and detected air quality, respectively. The horizontal axes for both graphs of the history data represent time, the vertical axis of FIG. 3B represents decibel or voltage amplitude, and the vertical axis of FIG. 3C represents air quality index. The history data of the detected sounds obtained during the learning mode is used to generate base data for identifying bullying or sleep apnea at the installation location in the active mode. As the detected sound fluctuates, the threshold value for identification may vary according to the times. For example, the threshold value for detecting bullying at dawn may be lower than the threshold value for detecting bullying at noon. It may also vary based on the day of week and location. The threshold value on Wednesday may be higher than on Sunday at a school. On the other hand, the threshold value on Wednesday may be lower than on Sunday at a commercial establishment such as a department store.

In an aspect, the detection sensors 110 may repeat the learning mode and active mode consecutively. As shown in FIG. 3C, the first period (e.g., about ten seconds from the start to 09:31:38) may be used in the learning mode to collect data regarding the environment. Then, the detection sensor 110 determines whether an adjustment or calibration needs to be made to the modified hydrogen sensor so as to properly detect vaping. For example, the voltage or resistance in the modified hydrogen sensor varies depending on temperature of the environment. Thus, the modified hydrogen sensor can be adjusted or calibrated based on the environment.

After the first period for collecting environment-calibrated data, the threshold value for vaping is determined in the active mode for a second period and the detection sensor 110 detects vaping based on the threshold value.

In another aspect, the detection sensors 110 may iterate the learning mode and the active mode after the first and second periods, meaning that the detection sensors 110 may calibrate the modified hydrogen sensor repeatedly so that the detection sensor 110 may accurately detect vaping.

FIG. 3C shows two curves. The upper curve represents threshold index value for identifying vaping. The lower curve represents the history data of detection results from the air quality sensor of the detection sensor 110. The upper curve is stabilized in a period of time after the power-up.

In an aspect, the detection sensors 110 may repeat the learning mode and active mode consecutively. As shown in FIG. 3C, the first period (e.g., about ten seconds from the start to 09:31:38) may be used in the learning mode to collect data regarding the environment. Then, the detection sensor 110 determines whether an adjustment or calibration needs to be made to the modified hydrogen sensor so as to properly detect vaping. For example, the voltage or resistance in the modified hydrogen sensor varies depending on temperature of the environment. Thus, the modified hydrogen sensor can be adjusted or calibrated based on the environment.

After the first period for collecting environment-calibrated data, the threshold value for vaping is determined in the active mode for a second period and the detection sensor 110 detects vaping based on the threshold value.

In another aspect, the detection sensors 110 may iterate the learning mode and the active mode after the first and second periods, meaning that the detection sensors 110 may calibrate the modified hydrogen sensor repeatedly so that the detection sensor 110 may accurately detect vaping based on the index value.

The index value is calculated based on the temperature, moisture, and the detection results of the modified hydrogen sensor. For example, the temperature falls in a range between 60 and 80 degree Fahrenheit, the moisture is increased by at least 10 percent, and the hydrogen increases from the base level (e.g., environment level) by approximately 10 percent, the detection sensor 110 may determine that vaping has occurred. This determination is provided as an example and is not provided to limit the scope of this application.

In an aspect, the control server 120 may send a command to the detection sensor 110 to adjust internal parameters for detecting bullying and vaping based on the trend identified from the history data. Further, the control server 120 may communicate with the detection sensors 110 by calling functions of application programming interface ("API") between the detection sensor 110 and the control server 120. In this regard, the detection sensor 110 can push detection results to the control server 120 and respond to the control server 120's request.

In an aspect, the control server 120 may not store detected results from the detection sensors 110 because of privacy issues. Nevertheless, the control sever 120 may provide signals back to the detection sensors 110 to indicate tuning parameters and false positives.

Internal parameters of the detection sensor 110 may include LED functionality, sound threshold, networking server IP address, alert timeout, serial number, reboot for device required or not, latest binary code, vape identification algorithm parameters. This list of parameters should not be understood as exhaustive but provided only for example purposes. The internal parameters of the detection sensor 110 may further include bullying identification algorithm parameters. Bullying or vaping identification algorithm parameters may include a window size or threshold values or ranges.

In an aspect, the control server 120 may update internal parameters via text or binary files. Internal parameters for each the detection sensor 110 may be saved in the database 130.

In another aspect, the control server 120 may control the detection sensors 110 collectively, individually, or group by group. For example, several the detection sensors 110 may be installed at the same site. When they need to update internal parameters or settings, the control server 120 may control the detection sensors 110 collectively at the site. However, such control may not affect the detection sensor 110 installed in the other sites. The control server 120 may use a query language to request data from the database 130. The query language may be SQL, MySQL, SSP, C, C++, C#, PHP, SAP, Sybase, Java, JavaScript, or any language, which can be used to request data from a database.

In yet another aspect, even when several detection sensors 110 are installed at the same site, the control server 120 may control them differently because one the detection sensor 110 may have different parameters for identifying bullying and vaping from those of another the detection sensor 110 due to different installation locations at the site. For example, the detection sensor 110 installed at a bedroom has parameters different from those of the detection sensor 110 installed at a bathroom.

Clients 170 may log in to the control server 120 to see graphical representations of the detection results from the detection sensor 110 via Internet. Communication between the clients 170 and the control server 120 may utilize http, https, ftp, SMTP, or related Internet protocols. The clients 170 may be able to adjust settings for each the detection sensor 110. For example, the settings may include a mode of warnings (e.g., an email, text message, telephone call, instant message, audible warning, etc.), an address, to which such warnings are to be sent in case of identification of bullying or vaping, and the like. The clients 170 are the ones who are responsible for the sites where the detection sensors 110 are installed for identifying bullying and vaping. For example, the clients 170 may be a principal, vice president, or person in charge at a school, a president at a company, a manager at a hospital or any commercial establishment, or security personnel. This list, however, is not meant to be exhaustive but is provided only for showing examples. Other peoples in different rankings, at different locations can be included in this list.

When the detection sensor 110 identifies bullying or vaping, the detection sensor 110 may send an alert to the clients 170 via a client server 160 using protocols of Internet. The client server 160 may be used for sending a simple message or email to the clients 170 supervising the site, where the bullying or vaping is detected. The client server 160 may manage the clients 160 registered on the client server 160 and show alert history and other notification upon requests from the clients 160. Further, the client server 160 may handle customizing or fine tuning the detection sensors 110, which lead to an alert when the detection sensors 110 need to reboot, update, or receive configuration. In an aspect, as dotted lines are shown in FIG. 1, the communication between the client server 160 and the clients 170 may not be regularly performed but can be made only when bullying or vaping is identified. The clients 170 may receive the alert on a computer, smart device, or mobile phone. In this way, the clients 170 are not swamped by overwhelming number of messages because they receive the alert only when bullying or vaping is identified. Further, the clients 170 may be able to timely, properly supervise at the site whenever an alert is received.

When the client server 160 receives an alert from the detection sensor 110, the client server 160 may communicate with the message server 140, which manages pushing alerts to the notification subscribers 150. The clients 170 may be the persons in charge as the first contact person who has a direct access to the control server 120 for the site, and the notification subscribers 150 may be any related personnel as the second contact persons who do not have a direct access to the control server 120. Similar to the ways the client server 160 sends alerts to the clients 170, the message server 140 sends alerts to the notification subscribers 150 via a text message, email, instant message, telephone call, audible warning, any communication means readily available to a person having skill in the art. The notification subscribers 150 may receive alerts via a computer, smart device, mobile phone, personal digital assistant, tablet, or any available means for receiving such alerts.

As described above, vaping can be identified when the signature is detected, meaning that vaping can be identified independent of locations and times. Thus, features related to identification of vaping may be integrated into the detection sensor 110. In this case, when vaping is identified, the detection sensor 110 may bypass the control server 120 and directly communicate with the message server 140 and the client server 160 to transmit alerts to ones in charge or responsible for the sites where the detection sensor 110 are installed. On the other hand, identification of bullying is different from site to site due to different environments. In other words, when sounds are detected by the detection sensor 110, the control server 120 receives and analyzes the detected sounds, and determines whether bullying has occurred. As a result, vaping may be identified earlier than bullying, and alerts for vaping may be sent to the notification subscribers 150 and the clients 170 faster than alerts for bullying.

In an aspect, features for identifying bullying may be also integrated into the detection sensor 110. This can be done by the control server 120 controlling the detection sensor 110 to update internal parameters for identifying bullying at the corresponding site. In this case, the control server 120 regularly checks the history data stored at the database 130 and regularly update the internal parameters of the detection sensor 110 for identifying bullying. After updating the internal parameters of the detection sensor 110, alerts for identifying bullying may be sent to the notification subscribers 150 and the clients 170 in the same way as alerts for identifying vaping are sent.

Now referring back to FIG. 2, a functional block diagram of the detection sensor 110 of FIG. 1 is shown in accordance with embodiments of the present disclosure. The detection sensor 110 may include a sound sensor 210, an air quality sensor 220, a network interface 230, a power unit 240, and a controller 250. The sound sensor 210 may be used for detecting sound and the air quality sensor 220 may be used for detecting air quality.

In particular, the sound sensor 210 detects sound levels (e.g., decibel (dB)) in the environment. For example, FIG. 3A shows detected sound levels in the form of voltage amplitudes. The horizontal axis represents time and the vertical axis represents voltage amplitude. Curves represent detected sound levels in voltage. The bold lines represent windows for identification. For example, the window of identification may be less than 1 second. Within the window, when the voltage amplitude is greater than a threshold value, bullying may be identified. In this example, the threshold value is about 4.9 volts. Thus, between 4 and 5 seconds, bullying may be identified.

As described above, the threshold value for identifying bullying depends on the installation location at the site and based on history data obtained during the learning mode. Since the detection sensor 110 may cover a limited area, several satellite detection sensors 110 may be installed at one enclosed space when the area of the enclosed space is greater than the area each satellite detection sensor 110 can cover. For example, the detection sensor 110 may cover an area of 10 by 10 square feet. In this situation, each satellite detection sensor 110 may have different threshold value for identifying bullying due to different installation locations at the same enclosed space. The air quality sensor 220 may detect air quality including moisture and hydrogen content in the air and temperature of the air. In other words, the air quality sensor 220 may include a combination of sensors sensing air quality. In an aspect, the air quality sensor 220 may include other sensors sensing air content of the environment. Vaping may be detected by specific range combination of humidity, hydrogen, and temperature, which is defined as signature in this disclosure. Since the signature does not depend on installation locations and times, internal parameters for identifying vaping may be predetermined. In other words, the air quality sensor 220 does not need training, while the sound sensor 210 needs training. The network interface 230 may be configured to transmit sensed results to the control server 120. In an aspect, the network interface 230 may transmit a request to send an alert, when bullying or vaping is identified, to the message server 140 and the client server 160. Further, the network interface 230 may receive a command to update internal settings or parameters from the control server 120.

In an aspect, the network interface 230 may communicate with others wirelessly or via a wired connection. Wireless connections may be wide area network (WAN), local area network (LAN), personal area network (PAN), ad hoc network, cellular network, etc. Wired network may utilize category 5 cable (CAT5), CAT5E, category 6 cable (CAT6), or similar cables. The sound sensor 210, the air quality sensor 220, and the network interface 230 may be powered by the power unit 240. Regular batteries may be installed to supply power to the detection sensor 110. For example, AA, AAA, or other suitable batteries may be used. The power unit 240 may utilize batteries and a connection to a power outlet so that the power unit 240 may supply power by using the batteries just in case when the power is out.

In an aspect, the power unit 240 may receive power supplied from a network cable, such as CAT5 or CAT6, which is called power-over-Ethernet (PoE) or active Ethernet. PoE+ and 4PPoE may be also used to supply power. Since the network cable supplies power, the detection sensor 110 may be installed everywhere the network cable can be installed without worrying about a distance to a power outlet. Also, since the power unit 240 does not need electric components necessary for connections to a power outlet, manufacturing cost can be lowered and the size of the detection sensor 110 can be reduced. The detection sensor 110 further includes the controller 250, which controls functions and settings of the detection sensor 110. When the detection sensor 110 is powered, the controller 250 sets settings of the detection sensor 110 and internal parameters of the sound sensor 210 and the air quality sensor 220. The controller 250 further controls the network interface 230 to transmit detected results or requests for sending alerts when bullying, sleep apnea, or vaping is detected, and reset or update settings and internal parameters upon reception of update command from the control server 120.

The controller 250 may be implemented on Linux, Windows, android, IOS, or similar software operation system. In an aspect, the controller 250 may be implemented on a hardware system, such as a digital signal processor (DSP), application-specific integrated circuit (ASIC), field-programmable gate array (FPGA), different types of programmable read-only memory (e.g., PROM, EPROM, EEPROM, etc.), or microprocessor such as Raspberry Pi.

In an aspect, the controller 250 may be implemented on a hardware system by removing unnecessary features from the hardware system to reduce power consumption and integrating necessary features for identification into the hardware system. For example, the controller 250 may be implemented on a Raspberry Pi by removing unnecessary features, which were already equipped in the Raspberry Pi, and by integrating features for identifying vaping. In this way, power required for running the sound sensor 210, the air quality sensor 220, the network interface 230, and the controller 250 can be sufficiently supplied via a network cable. This approach for reducing power consumption may be applied to other hardware systems or software operating systems.

In an aspect, the detection sensor 110 may not be equipped with a warning system. Thus, when bullying or vaping is detected at the installation site, any person who bullies or vapes cannot recognize that the identification of such is reported to the clients 170 and the notification subscribers 150 because the identification is reported silently to the person.

Figure 4:
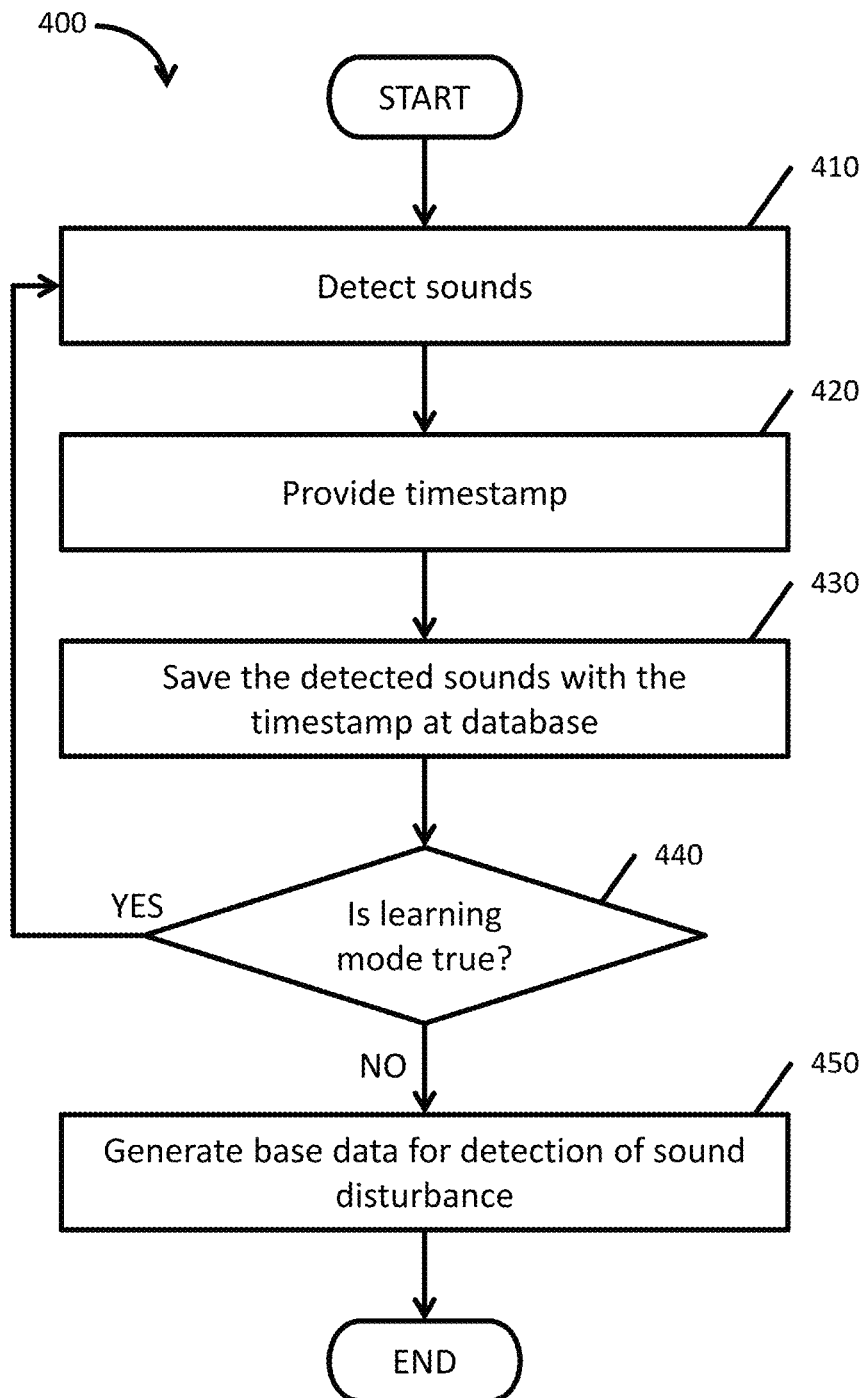
FIG. 4 is a flowchart showing a learning mode for the detection sensor in accordance with embodiments of the present disclosure.

FIG. 4 shows a flowchart for a method 400 in the learning mode in accordance with embodiments of the present disclosure. As described above, the sound sensor 210 of the detection sensor 110 needs training to generate base data. In the learning mode, the base data is generated. In step 410, the sound sensor detects sounds for a predetermined period. The detected sound is combined with the corresponding timestamp in step 420. The timestamp may include the time, the day of the week, the day, and the month when the sound is detected. The combined data is then saved in a database in step 430.

In step 440, it is checked whether or not the learning mode is still true. If it is true, the method 400 repeats steps 410-440 until sufficient sound data is saved in the database. In an aspect, the sound data may be saved in a memory in the detection sensor 110 but not in the data base, which is distant from the detection sensor 110, for protecting privacy.

If it is determined that the learning mode is false in step 440, the method 400 proceeds to step 450, in which base data is generated based on the detected sounds saved at the database during the learning mode. The base data may include a series of threshold values for identifying bullying or sleep apnea along the time of each day, each week, or each month depending on the total duration of the learning mode. After generation of the base data, the method 400 ends.

Figure 5:
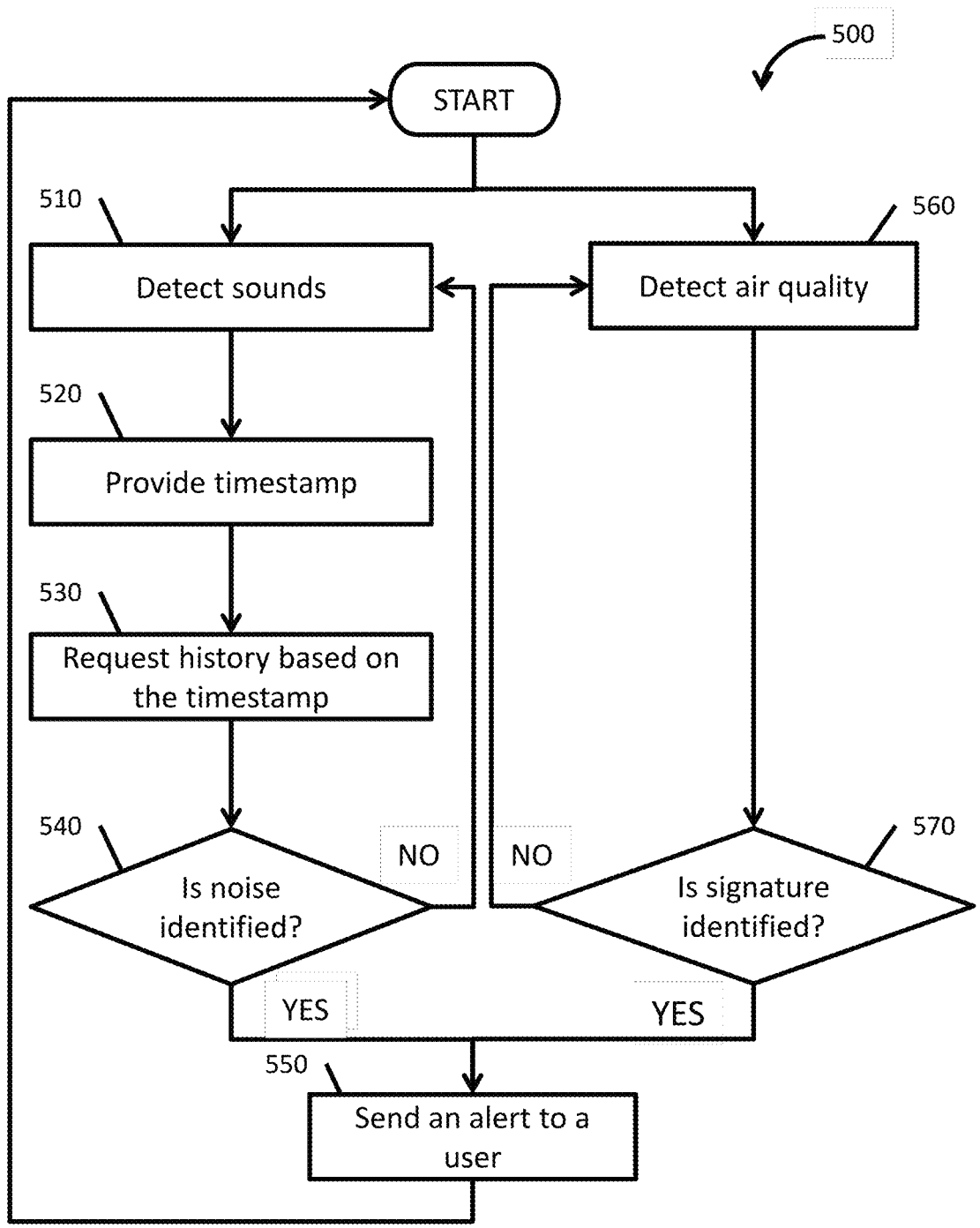
FIG. 5 is a flowchart showing an active mode for the detection sensor in accordance with embodiments of the present disclosure.

Now turning to FIG. 5, a method 500 is provided in the active mode in accordance with embodiments of the present disclosure. After the base data is generated in method 400 of FIG. 4, the method 500 starts with steps 510 and 560. In step 510, the sound sensor detects sound in the environment and in step 560, the air quality sensor detects air quality. In the method 500, detections of sound and air quality are shown parallelly. In an aspect, such detections may be serially performed.

In step 520, timestamp is provided to the detected sounds. Based on the timestamp, a control system makes a request for history data from the database in step 530. The control system then determines based on the history data whether or not noise disturbance is detected in step 540. The noise disturbance may be related to bullying or sleep apnea. In an aspect, the noise disturbance may be related to sound related phenomena or situations, such as fights, hurricane, voice recognition, etc.

If it is determined that the noise disturbance is identified in step 540, the control system silently sends an alert to one or more users who are in charge of the installation site in step 550. After sending the alert, the method 500 restarts the process.

If it is determined that the noise disturbance is not identified in step 540, steps 510-550 are repeated.

Now returning back to the air quality detection, after the air quality is detected in step 560, the control system determines whether or not the signature is identified in step 570. If it is determined that the signature is identified in step 570, the control system silently sends an alert to the one or more users via a text message, email, instant message, optical warning, or oral warning in step 550.

In case when it is determined that the signature is not identified in step 570, the method 500 repeats steps 560 and 570. In this way, sleep apnea, bullying, or vaping can be detected and informed to the users. Peoples at the site, however, may not acknowledge the transmission of the alert because the alert is transmitted silently to the people at the site.

Figure 6:
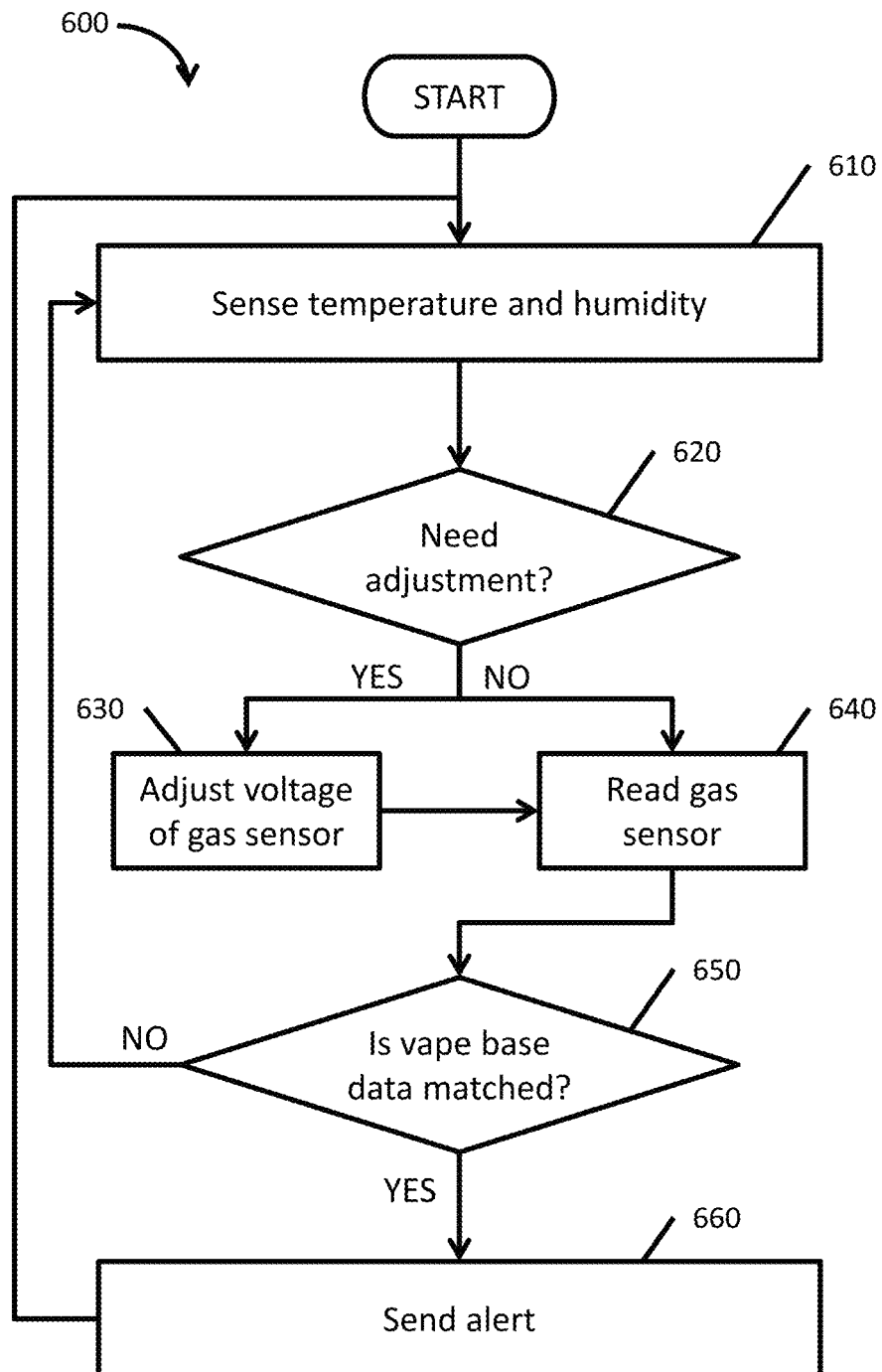
FIG. 6 is a flowchart showing a method for detecting vaping in accordance with embodiments of the present disclosure.

Turning now to FIG. 6, a flowchart is provided for a method 600 for detecting vape. The method starts from sensing temperature and humidity in step 610. As described above, the modified hydrogen sensor of the detection sensor may vary because the voltage or resistance in the modified hydrogen sensor varies depending on temperature of the environment. Thus, in step 620, it is determined whether an adjustment to the modified hydrogen sensor is needed.

When it is determined that the adjustment is needed in step 620, the voltage or resistance of the modified hydrogen sensor is adjusted to appropriately sense gas (e.g., hydrogen) in step 630 and then the method 600 moves to step 640.

When it is determined that the adjustment is not needed in step 620, the modified gas sensor reads gas in step 640.

In step 650, it is determined whether the sensed temperature, humidity, and gas match abnormality matching signature, meaning that the sensed results are within the corresponding ranges. When they match the abnormality matching signature, an alert is sent in step 660. Otherwise, the method 600 goes back to step 610 and repeats steps 610-660.

Figure 7:
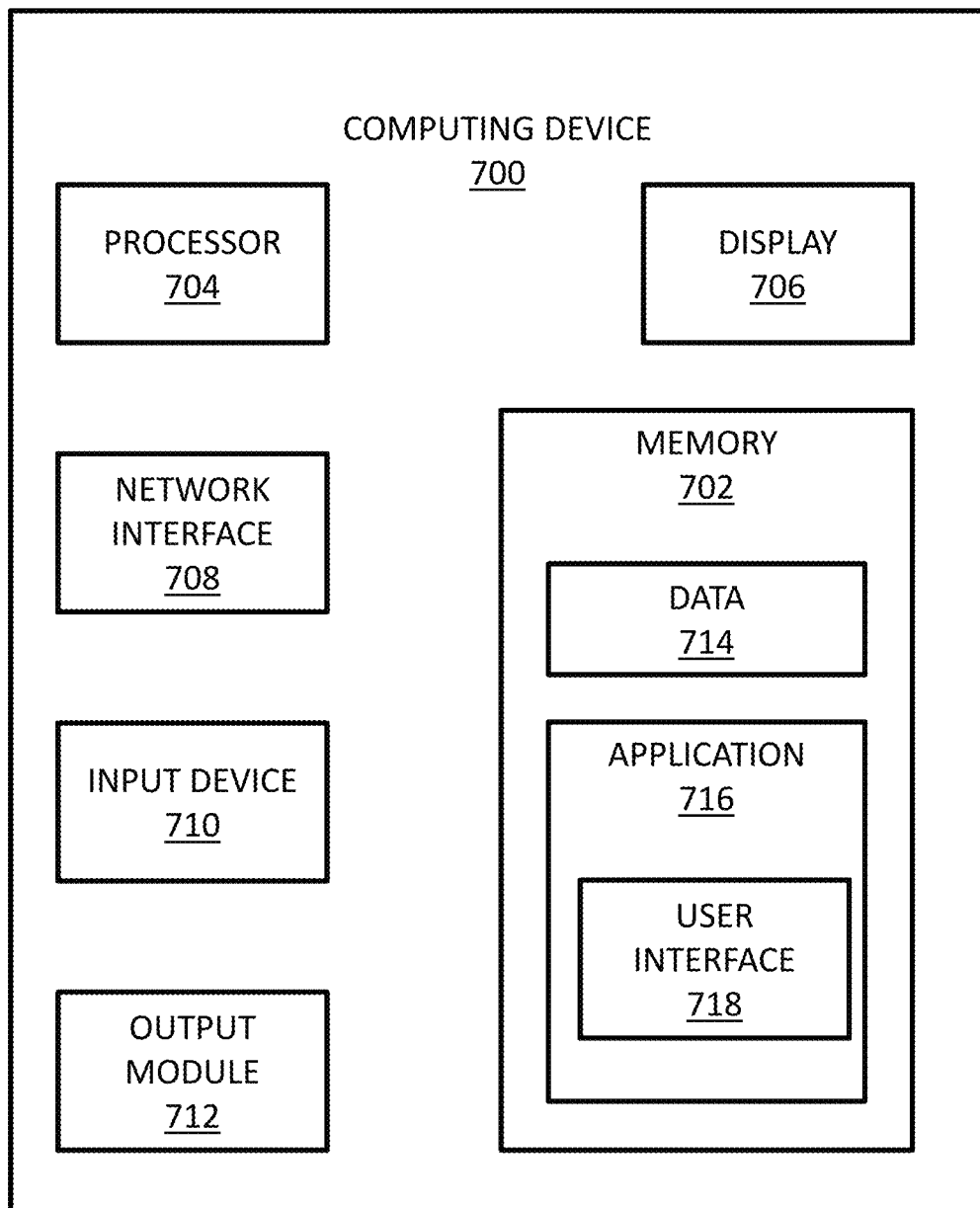
FIG. 7 is a functional block diagram of a computing device in accordance with embodiments of the present disclosure.

Turning now to FIG. 7, a simplified block diagram is provided for a computing device 700, which can be implemented as the control server 120, the database 130, the message server 140, and the client server 160 of FIG. 1. The computing device 700 may include a memory 702, a processor 704, a display 706, a network interface 708, an input device 710, and/or an output module 712. The memory 702 includes any non-transitory computer-readable storage media for storing data and/or software that is executable by the processor 704 and which controls the operation of the computing device 700.

In an aspect, the memory 702 may include one or more solid-state storage devices such as flash memory chips. Alternatively or in addition to the one or more solid-state storage devices, the memory 702 may include one or more mass storage devices connected to the processor 704 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 704. That is, computer readable storage media may include non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the computing device 700.

Figure 2:
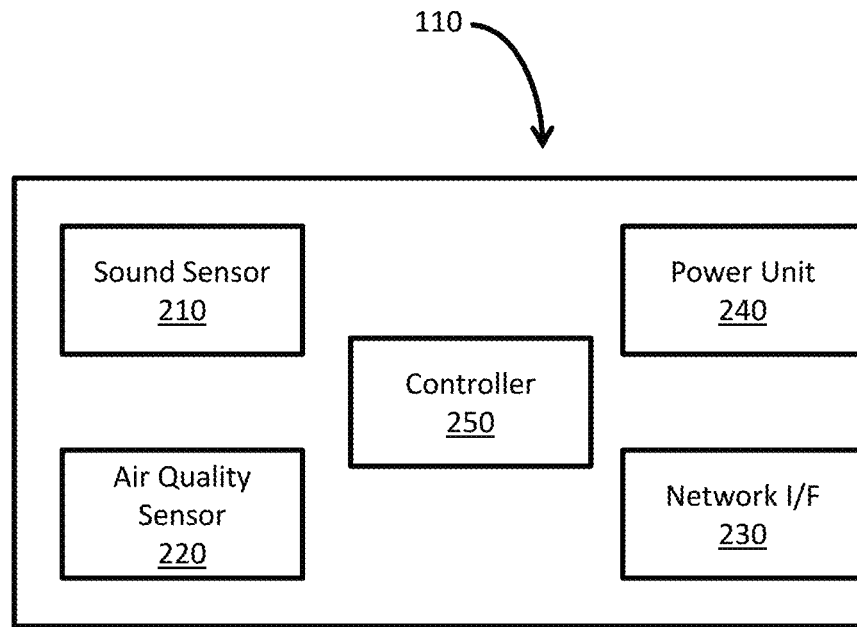
FIG. 2 is a functional block diagram of the detection sensor of FIG. 1 in accordance with embodiments of the present disclosure.

The memory 702 may store application 716 and/or data 714 (e.g., base data and history data from the sound sensor 210 and the air quality sensor 220 of FIG. 2). The application 716 may, when executed by processor 704, cause the display 706 to present the user interface 718 including FIGS. 3A-3C. The processor 704 may be a general purpose processor, a specialized graphics processing unit (GPU) configured to perform specific graphics processing tasks while freeing up the general purpose processor to perform other tasks, and/or any number or combination of such processors. The display 706 may be touch-sensitive and/or voice-activated, enabling the display 706 to serve as both an input and output device. Alternatively, a keyboard (not shown), mouse (not shown), or other data input devices may be employed. The network interface 708 may be configured to connect to a network such as a local area network (LAN) consisting of a wired network and/or a wireless network, a wide area network (WAN), a wireless mobile network, a Bluetooth network, and/or the internet.

For example, the computing device 700 may receive, through the network interface 708, detection results for the detection sensor 110 of FIG. 1, for example, detected sound in the learning mode and the active mode, and history data, which is time-series data including detected sounds and detected air quality from the detection sensor 110 for the whole running times or a predetermined period. The computing device 700 may receive updates to its software, for example, the application 716, via the network interface 708. The computing device 700 may also display notifications on the display 706 that a software update is available.

The input device 710 may be any device by means of which a user may interact with the computing device 700, such as, for example, a mouse, keyboard, foot pedal, touch screen, and/or voice interface. The output module 712 may include any connectivity port or bus, such as, for example, parallel ports, serial ports, universal serial busses (USB), or any other similar connectivity port known to those skilled in the art. The application 716 may be one or more software programs stored in the memory 702 and executed by the processor 704 of the computing device 700. The application 716 may be installed directly on the computing device 700 or via the network interface 708. The application 716 may run natively on the computing device 700, as a web-based application, or any other format known to those skilled in the art.

In an aspect, the application 716 will be a single software program having all of the features and functionality described in the present disclosure. In other aspect, the application 716 may be two or more distinct software programs providing various parts of these features and functionality. Various software programs forming part of the application 716 may be enabled to communicate with each other and/or import and export various settings and parameters relating to the identification of bullying, sleep apnea, and vaping. The application 716 communicates with a user interface 718 which generates a user interface for presenting visual interactive features to the notification subscribers 150 or the clients 170 of FIG. 1 on the display 706. For example, the user interface 718 may generate a graphical user interface (GUI) and output the GUI to the display 706 to present graphical illustrations such as FIGS. 3A-3C.

Since other modifications and changes may be made to fit particular operating requirements and environments, it is to be understood by one skilled in the art that the present disclosure is not limited to the examples described in the present disclosure and may cover various other changes and modifications which do not depart from the spirit or scope of this disclosure.

What is claimed is:

1. A sensor system for identifying vaping, other smoking activities, and bullying at a site, the sensor system comprising:
   an air quality sensor configured to detect air quality;
   a sound detector configured to detect sounds; and
   a control server configured to analyze abnormality matching signature of vaping, other smoking activity, and sound of bullying based on data stored at a database, to determine whether vaping, smoking, or bullying occurs at the site, and to transmit an alert via a network interface when an occurrence of vaping, smoking, or bullying at the site is determined,
   determined wherein the bullying is determined based on the detected sound,
   wherein the vaping or the other smoking activity is determined when the detected air quality includes a portion of the abnormality matching signature, and
   wherein the portion of the abnormality matching signature includes a temperature range, a hydrogen range, and a humidity range.

2. The sensor system according to claim 1, wherein the sensor system is powered via power over Ethernet or power over Ethernet+, or powered by a power outlet.

3. The sensor system according to claim 2, wherein the power is supplied by a CAT5, CAT5E, or CAT6 cable.

4. The sensor system according to claim 3, wherein the detected air quality and the detected sounds are transmitted via the CAT5, CAT5E, or CAT6 cable, or wireless via WiFi or cellular.

5. The sensor system according to claim 1, wherein the air quality sensor is location-independent.

6. The sensor system according to claim 1, wherein the sound detector is location-dependent.

7. The sensor system according to claim 6, wherein the sound detector is to detect sounds in a predetermined period in a learning mode prior to identification of the bullying.

8. The sensor system according to claim 7, wherein the detected sounds during the predetermined period generate base data for identifying the bullying at the site.

9. The sensor system according to claim 8, wherein the bullying is determined when the detected sounds are greater than or equal to a threshold value based on environment calibrated data.

10. The sensor system according to claim 1, wherein an alert is transmitted from the site at the site to a user when the vaping, another smoking activity, or bullying is detected.

11. The sensor system according to claim 10, wherein the alert is a text message, an email, an optical flashing, an audible sound, or combination thereof.

12. The sensor system according to claim 1, wherein the sensor system is run by a mobile operating system.

13. An identification system for identifying vaping, other smoking activities, and bullying, the system comprising:
   a sensor system disposed at a site, the sensor system comprising:
      an air quality sensor configured to detect air quality; and
      a sound detector configured to detect sounds; and
   a controller coupled to the sensor system via a network and configured to analyze abnormality matching signature of vaping and other smoking activity based on data stored at a database, determine whether bullying or smoking activity occurs at the site, and transmit an alert to a user via a network interface when an occurrence of bullying or smoking activity is determined,
   wherein the vaping or another smoking activity is determined when the detected air quality includes the abnormality matching signature, and
   wherein the abnormality matching signature includes a temperature range, a hydrogen range, and a humidity range.

14. The identification system according to claim 13, wherein the sensor system is powered via power over Ethernet or power over Ethernet+.

15. The identification system according to claim 14, wherein the power is supplied by a CAT5, CAT5E, or CAT6 cable.

16. The identification system according to claim 15, wherein the detected air quality and the detected sounds are transmitted via the CAT5, CAT5E, or CAT6 cable, or wireless via WiFi or cellular.

17. The identification system according to claim 13, wherein the air quality sensor is location independent.

18. The identification system according to claim 13, wherein the sound detector is location dependent.

19. The system according to claim 18, wherein the sound detector is to detect sounds in a predetermined period in a learning mode prior to identification of the noise disturbance.

20. The identification system according to claim 19, wherein the detected sounds during the predetermined period generate base data for the bullying at the enclosed site.

21. The identification system according to claim 20, wherein the bullying is determined when the detected sounds are greater than or equal to a threshold value based on the base data.

22. The identification system according to claim 13, wherein the alert is transmitted silently from the site to a user when the vaping, another smoking activity, or bullying is determined.

23. The identification system according to claim 22, wherein the alert is a text message, an email, an optical flashing, an audible sound, or combination thereof.

24. The identification system according to claim 13, wherein the sensor system is run by a mobile operating system.

25. The identification system according to claim 13, wherein the alert is transmitted silently from the site to a user when the vaping, another smoking activity, or bullying is determined.

26. The identification system according to claim 25, wherein the alert is a text message, an email, an optical flashing, an audible sound, or combination thereof.

27. A sensor system for identifying vaping, other smoking activities, and bullying at a site, the sensor system comprising:
an air quality sensor configured to detect air quality;
a sound detector configured to detect sounds; and
a control server configured to analyze abnormality matching signature of vaping, smoking activity, and sound of bullying based on data stored at a database, determine whether bullying, smoking activity, or bullying occurs, and transmit an alert via a network interface when an occurrence of vaping, smoking activity, or bullying is determined,
wherein the vaping or another smoking activity is identified determined based on the detected air quality,
wherein the bullying is determined based on the detected sound,
wherein the sound detector is location-dependent,
wherein the sound detector is to detect sounds in a predetermined period in a learning mode prior to determination of the bullying,
wherein the detected sounds during the predetermined period generate base data for determining the bullying at the site, and
wherein the bullying is determined when the detected sounds are greater than or equal to a threshold value based on environment calibrated data.

28. The sensor system according to claim 27, wherein the sensor system is powered via power over Ethernet or power over Ethernet+, or powered by a power outlet.

29. The sensor system according to claim 28, wherein the power is supplied by a CAT5, CAT5E, or CAT6 cable.

30. The sensor system according to claim 29, wherein the detected air quality and the detected sounds are transmitted via the CAT5, CAT5E, or CAT6 cable, or wireless via WiFi or cellular.

31. The sensor system according to claim 27, wherein the vaping or the other smoking activity is determined when the detected air quality includes the abnormality matching signature.

32. The sensor system according to claim 31, wherein the abnormality matching signature includes a temperature range, a hydrogen range, and a humidity range.

33. The sensor system according to claim 27, wherein the air quality sensor is location-independent.

34. The sensor system according to claim 27, wherein an alert is transmitted from the site at the site to a user when the vaping, another smoking activity, or bullying is detected.

35. The sensor system according to claim 34, wherein the alert is a text message, an email, an optical flashing, an audible sound, or combination thereof.

36. The sensor system according to claim 27, wherein the sensor system is run by a mobile operating system.

37. An identification system for identifying vaping, other smoking activities, and bullying, the system comprising:
a sensor system disposed at a site, the sensor system comprising:
an air quality sensor configured to detect air quality; and
a sound detector configured to detect sounds; and
a controller coupled to the sensor system via a network and configured to analyze abnormality matching signature of vaping, other smoking activity, and sound of bullying based on data stored at a database, determine whether vaping, smoking activity, and bullying occurs at an enclosed site, and to transmit an alert to a user via a network interface when an occurrence of vaping, smoking activity, or bullying is determined, and
wherein the sound detector is location dependent,
wherein the sound detector is to detect sounds in a predetermined period in a learning mode prior to determination of the noise disturbance,
wherein the detected sounds during the predetermined period generate base data for the bullying at the enclosed site, and
wherein the bullying is determined when the detected sounds are greater than or equal to a threshold value based on the base data.

38. The identification system according to claim 37, wherein the sensor system is powered via power over Ethernet or power over Ethernet+.

39. The identification system according to claim 38, wherein the power is supplied by a CAT5, CAT5E, or CAT6 cable.

40. The identification system according to claim 39, wherein the detected air quality and the detected sounds are transmitted via the CAT5, CAT5E, or CAT6 cable, or wireless via WiFi or cellular.

41. The identification system according to claim 37, wherein the vaping or another smoking activity is determined when the detected air quality includes the abnormality matching signature.

42. The identification system according to claim 41, wherein the abnormality matching signature includes a temperature range, a hydrogen range, and a humidity range.

43. The identification system according to claim 37, wherein the air quality sensor is location independent.

44. The identification system according to claim 37, wherein the sensor system is run by a mobile operating system.

* * * * *